US011406604B2

(12) United States Patent
Corne et al.

(10) Patent No.: US 11,406,604 B2
(45) Date of Patent: Aug. 9, 2022

(54) NANOCAPSULES AND METHOD FOR MANUFACTURING THEREOF

(71) Applicant: LUXEMBOURG INSTITUTE OF SCIENCE AND TECHNOLOGY (LIST), Esch-sur-Alzette (LU)

(72) Inventors: Gaelle Corne, Audun-le-Tiche (FR); Jean-Sebastien Thomann, Gorcy (FR)

(73) Assignee: LUXEMBOURG INSTITUTE OF SCIENCE AND TECHNOLOGY (LIST), Esch-sur-Alzette (LU)

( * ) Notice: Subject to any disclaimer, the term of this patent is extended or adjusted under 35 U.S.C. 154(b) by 93 days.

(21) Appl. No.: 16/478,173

(22) PCT Filed: Jan. 17, 2018

(86) PCT No.: PCT/EP2018/051060
§ 371 (c)(1),
(2) Date: Jul. 16, 2019

(87) PCT Pub. No.: WO2018/134222
PCT Pub. Date: Jul. 26, 2018

(65) Prior Publication Data
US 2019/0365660 A1    Dec. 5, 2019

(30) Foreign Application Priority Data

Jan. 20, 2017  (LU) ..................................... 100023

(51) Int. Cl.
*A61K 9/51* (2006.01)
*A61K 9/127* (2006.01)
*A61K 49/00* (2006.01)

(52) U.S. Cl.
CPC .......... *A61K 9/5192* (2013.01); *A61K 9/1271* (2013.01); *A61K 9/1277* (2013.01); *A61K 9/5115* (2013.01); *A61K 9/5123* (2013.01); *A61K 9/5161* (2013.01); *A61K 49/0093* (2013.01)

(58) Field of Classification Search
None
See application file for complete search history.

(56) References Cited

U.S. PATENT DOCUMENTS 8,992,984 B1    3/2015  Brinker et al.
2015/0272885 A1  10/2015  Ashley et al.

FOREIGN PATENT DOCUMENTS

| WO | 2010078569 A2 | 7/2010 | |
|----|----|----|----|
| WO | 2014138278 A1 | 9/2014 | |
| WO | WO-2014165608 A1 * | 10/2014 | ......... A61K 31/5383 |
| WO | 2017013250 A1 | 1/2017 | |
| WO | 2017017022 A1 | 2/2017 | |

OTHER PUBLICATIONS

International Search Report for corresponding PCT/EP2018/051060, dated Apr. 18, 2018.
Dai Etal: "Factors affecting protein release from microcapsule prepared by liposome in alginate", Colloids and Surfaces B: Biointerfaces, 2005, 42, 253-258).
Cuomo Etal: "pH-responsive liposome-templated polyelectrolyte nanocapsules" (Soft Matter, 2012, 8, 4415-4420).
Cuomo Etal: "Loading and protection of hydrophilic molecules into iposome-templated polyelectrolyte nanocapsules" (Langmuir, 2014, 30, 7993-7999).

* cited by examiner

*Primary Examiner* — Jennifer Lamberski
(74) *Attorney, Agent, or Firm* — Sandberg Phoenix & von Gontard PC (57) ABSTRACT

A method for manufacturing supported lipid bilayer on a porous silica nanoparticle with a ζ-potential comprised between −10 mV and +10 mV, the method comprising the steps of (a) providing a negatively charged supported lipid bilayer on a porous silica nanoparticle, wherein the negatively charged supported lipid bilayer has a ζ-potential inferior to −15 mV and wherein the negatively charged supported lipid bilayer comprised at least one phospholipid and; (b) adding a formulation of lipids, the lipids being 1,2-dioleoyl-3-trimethylammonium-propane alias DOTAP, cholesterol and at least one lipid different from DOTAP and cholesterol. The method further comprises the step of (c) performing an ultra-sonication for promoting DOTAP incorporation. The method can be supplemented by the step of addition of alginate and the step of cross-linking the alginate. Also a nanocapsule and composition comprising the nanocapsule.

20 Claims, 3 Drawing Sheets

Fig. 1

| Samples | NTA Size in milliQ water (nm) | NTA Size in HEPES Buffer (nm) | NTA Size in Human Serum (nm) |
|---|---|---|---|
| MSNPs | 68 ± 36 | 127 ± 71 | 124 ± 66 |
| MSNPs+ | 99 ± 42 | 187 ± 83 | NA |
| SLB⁻@MSNPs | 127 ± 43 | 145 ± 69 | 139 ± 72 |

NANOCAPSULES AND METHOD FOR MANUFACTURING THEREOF

CROSS-REFERENCE TO RELATED APPLICATIONS

The present invention is the US national stage under 35 U.S.C. § 371 of International Application No. PCT/EP2018/01060, which was filed on Jan. 17, 2018, and which claims the priority of application LU 100023 filed on Jan. 20, 2017, the content of which (text, drawings and claims) are incorporated here by reference in its entirety.

FIELD

The invention is directed to the field of synthesis of porous silica nanomaterials adapted to be used as nanovector for the encapsulation and the delivery of materials.

BACKGROUND

Porous silica nanomaterials allow different biomedical applications such as drug delivery, therapeutic imaging, and diagnosis. In this context, porous and mesoporous silica nanoparticles (MSNPs) have been hugely studied as a vector for drug delivery applications.

Nanocapsules suitable for delivering an active moiety are known in the art as being protected by an outer layer. The outer layer can be for instance a supported lipid bilayer (SLB). This outer layer is important for the release properties of the nanocapsule.

Liposomes are artificial membranes composed mostly of phospholipids Cholesterol is often used in the preparation of liposome, in order to reduce the fluidity of the hydrocarbon chains and to make the liposomes less permeable. The liposomes alone cannot be used as nanocapsule, since they are very rapidly taken up by the immune system of an organism, which limits the duration for which the liposomes circulate and can release the entrapped active moiety inside the blood stream (see study entitled "Factors affecting protein release from microcapsule prepared by liposome in alginate", by Dai C. et al., Colloids and Surfaces B: Biointerfaces, 2005, 42, 253-258).

The study entitled "pH-responsive liposome-templated polyelectrolyte nanocapsules" (Cuomo F. et al., Soft Matter, 2012, 8, 4415-4420) relates to hollow nanocapsule made of polyectrolyetolytes. They are produced by implementing a layer-by-layer (LBL) approach, using liposomes as template. Negatively charged alginate and positively charged chitosan, two biocompatible polymers are alternatively adsorbed onto liposomes, producing nanocapsules with an average diameter of about 280 nm. When the outer layer is made of chitosan, the nanocapsules are stable only at acidic pH, while when the outer layer is made of alginate, the nanocapsules remain stable at a pH range comprised between 4.6 and 8.

The study entitled "Loading and protection of hydrophilic molecules into liposome-templated polyelectrolyte nanocapsules" (Cuomo F. et al, *Langmuir;* 2014, 30, 7993-7999) relates to structure with submicrometer dimension that can entrap dextran. The system shows an ability to retain the molecules both at slightly acidic or neutral pH and consists also of LBL approach, using liposomes as template and negatively charged alginate and positively charged chitosan.

Ideally, a controlled release active moiety system must have high encapsulation efficiency, must provide maximal stability and a low initial burst. It is however often difficult to provide a homogeneous outer layer of alginate, especially when supported lipid bilayer bearing a negative charge is surrounding the inner core of the nanocapsule, namely the porous silica nanoparticle. When trying to combine negatively charged alginate on negatively charged supported lipid bilayer, agglomeration issues occur and then, those nanocapsules often present leakage issues, leading to uncontrolled released of the active moiety, which renders them unsuitable for therapeutic, pharmaceuticals and/or other similar applications.

SUMMARY

The invention has for technical problem to alleviate at least one of the drawbacks present in the prior art.

More particularly, the invention has for technical problem to provide a biocompatible nanocapsule with an outer layer that is sufficiently resistant to prevent the leakage of the active moiety and to be sufficiently biodegradable at the same time to favour the slow and control release of the active moiety, especially when negatively charged alginate is to be designed as the outer layer of a nanocapsule surrounded by negatively charged lipid bilayer.

In general, the particular embodiments of each object of the invention are also applicable to other objects of the invention. To the extent possible, each object of the invention is combinable with other objects.

The first object of the invention is directed to a method for manufacturing supported lipid bilayer on a porous silica nanoparticle with a ζ-potential comprised between −10 mV and +10 mV, the method comprising the steps of (a) providing a negatively charged supported lipid bilayer on a porous silica nanoparticle, wherein the negatively charged supported lipid bilayer has a ζ-potential inferior to −15 mV and wherein the negatively charged supported lipid bilayer comprised at least one phospholipid and; (b) adding a formulation of lipids, the lipids being 1,2-dioleoyl-3-trimethylammonium-propane alias DOTAP, cholesterol and at least one lipid different from DOTAP and cholesterol. The method is remarkable in that it further comprises the step of (c) performing an ultra-sonication.

According to various embodiments, the step of (c) performing an ultra-sonication is achieved for promoting DOTAP incorporation.

According to various embodiments, the ultra-sonication is carried out at a temperature comprised between 40° C. and 60° C.

According to various embodiments, the concentration of DOTAP in the formulation of lipids is comprised between 50% and 150% of the concentration of the at least one phospholipid, in various instances in a concentration amounting to 100% of the concentration of the at least one phospholipid.

According to various embodiments, the at least one phospholipid is 1,2 dioleoyl-sn-glycero-3-phospho-L-serine alias DOPS.

According to various embodiments, the step of ultra-sonication is performed between 10 minutes and 30 minutes, in various instances during 20 minutes.

According to various embodiments, the at least one lipid different from DOTAP and cholesterol in step (b) is 1,2-dipalmitoyl-sn-glycero-3-phosphocholine alias DPPC.

The second object of the present invention is directed to a method for manufacturing a nanocapsule based on a supported lipid bilayer on a charged porous silica nanoparticle with a ζ-potential comprised between −10 mV and +10 mV, the method comprising the method in accordance with the first object of the invention and the steps of addition of an aqueous solution of sodium alginate; and of cross-linking of the sodium alginate.

According to various embodiments, the concentration of sodium alginate in the aqueous solution is comprised between 1% (wt %) and 5% (wt %), in various instances is equal to 2% (wt %).

According to various embodiments, the addition is performed in a buffer solution, the buffer solution being based on 4-(2-hydroxyethyl)-1-piperazineethanesulfonic acid alias HEPES or on phosphate-buffered saline alias PBS.

According to various embodiments, the step of cross-linking of the sodium alginate is performed by mixing an aqueous solution of divalent cation, in various instances calcium-based cation or barium-based cation, at a concentration comprised between 40 mM and 60 mM, in various instances at a concentration of 50 mM.

According to various embodiments, the porous silica nanoparticle is a mesoporous silica nanoparticle, in various instances a positively charged mesoporous silica nanoparticle.

The third object of the present invention is directed to a nanocapsule suitable for encapsulating at least one active moiety, the nanocapsule comprising an inner core, an inner layer and an outer layer, the inner core being formed by a porous silica nanoparticle, the inner layer being formed by a lipid bilayer, wherein the lipid bilayer comprised at least one phospholipid, characterized in that the outer layer comprises cross-linked sodium alginate.

According to various embodiments, the outer layer of cross-linked sodium alginate has a thickness comprised between 3 nm and 100 nm, in various instances between 20 nm and 30 nm, for example 25 nm.

According to various embodiments, the porous silica nanoparticle is a mesoporous silica nanoparticle, in various instances a positively charged mesoporous silica nanoparticle.

The fourth object of the invention is directed to a composition comprising the nanocapsule in accordance with the third object of the invention and at least one active moiety, the at least one active moiety being in the inner core of the nanocapsule.

According to various embodiments, the at least one active moiety is one contrasting agent in various instances selected from the group comprising calcein, rhodamine, methylene blue and indocyanine green, for example indocyanine green.

According to various embodiments, the composition comprising the nanocapsule in accordance with the third object of the invention, and at least one active moiety presenting therapeutic, pharmaceutical, nutraceutical and/or cosmeceutical properties, in various instances a molecule presenting anticancerous properties, the at least one active moiety presenting therapeutic, pharmaceutical, nutraceutical and/or cosmeceutical properties being in the inner core of the nanocapsule, is suitable for oral administration.

According to various embodiments, the composition comprising the nanocapsule in accordance with the third object of the invention, and at least one cosmetic agent, in various instances an antioxidant, and/or at least one dermatological agent, in various instances a wound-healing agent, the at least one cosmetic and/or dermatological agent being in the inner core of the nanocapsule, is suitable for topical administration.

According to various embodiments, the composition comprising the nanocapsule in accordance with the third object of the invention, and at least one active moiety presenting therapeutic and/or pharmaceutical properties, is suitable for loco-regional administration such as intraocular and/or intratumoral administration.

The fifth object of the invention is directed to a method for manufacturing a negatively charged supported lipid bilayer on a positively charged mesoporous silica nanoparticle, the method comprising the steps of (a) preparing a first formulation of lipids, the lipids from the first formulation being 1,2 dioleoyl-sn-glycero-3-phospho-L-serine alias DOPS, cholesterol and at least one lipid different from DOPS and cholesterol, the formulation of lipids being dissolved in a solvent; (b) evaporation the solvent; (c) adding an aqueous formulation of positively charged mesoporous silica nanoparticles; (d) performing a first ultra-sonication; (e) performing a centrifugation. The method is remarkable in that it further comprises the steps of (f) addition of a second formulation of lipids, the lipids from the second formulation being 1,2-dioleoyl-3-trimethylammonium-propane alias DOTAP, cholesterol and at least one lipid different from DOTAP and cholesterol, the second formulation of lipids being dissolved in a solvent; and (g) performing a second ultra-sonication; and wherein the negatively charged supported lipid bilayer on a positively charged mesoporous silica nanoparticle has a potential comprised between −10 mV and +10 mV.

According to various embodiments, the step of performing a second ultra-sonication is achieved for promoting DOTAP incorporation.

According to various embodiments, the number of equivalent of the DOTAP relative to one equivalent of DOPS is comprised between 0.5 and 1.5, in various instances is equal to 1.

According to various embodiments, the number of equivalents of cholesterol relative to one equivalent of DOPS is comprised between 2.30 and 2.70, in various instances is equal to 2.50.

According to various embodiments, the at least one lipid different from DOPS and cholesterol in step (a) is 1,2-dipalmitoyl-sn-glycero-3-phosphocholine alias DPPC.

According to various embodiments, the at least one lipid different from DOTAP and cholesterol in step (f) is 1,2-dipalmitoyl-sn-glycero-3-phosphocholine alias DPPC.

According to various embodiments, the number of equivalent of the DPPC relative to one equivalent of DOPS is comprised between 3.55 and 3.95, in various instances is equal to 3.75.

According to various embodiments, the solvent is a mixture of chloroform and methanol.

The sixth object of the invention is directed to a method for manufacturing a nanocapsule based on a negatively charged supported lipid bilayer on a positively charged mesoporous silica nanoparticle with a potential comprised between −10 mV and +10 mV, the method comprising the method in accordance with the fifth object of the invention followed by the steps of addition of an aqueous solution of sodium alginate; and the step of cross-linking of the sodium alginate.

According to various embodiments, the step of addition of alginate is performed by adsorption of an aqueous solution of sodium alginate at a concentration comprised between 1% (v/v) and 5% (v/v), in various instances at a concentration of 2% (v/v).

According to various embodiments, the step of cross-linking of the sodium alginate is performed by mixing an aqueous solution of calcium, at a concentration comprised between 40 mM and 60 mM, in various instances at a concentration of 50 mM.

The seventh object of the invention is directed to a nanocapsule suitable for encapsulating at least one active moiety, the nanocapsule comprising an inner core, an inner layer and an outer layer, the inner core being formed by a mesoporous silica nanoparticle, the inner layer being formed by a lipid bilayer. The nanocapsule is remarkable in that the outer layer comprises cross-linked sodium alginate.

According to various embodiments, the outer layer of cross-linked sodium alginate has a thickness comprised between 3 nm and 100 nm, in various instances between 20 nm and 30 nm, for example 25 nm.

The eighth object of the invention is directed to a composition comprising the nanocapsule in accordance with the seventh object of the invention and at least one active moiety, the at least one active moiety being in the inner core of the nanocapsule.

According to various embodiments, the at least one active moiety is a contrasting agent in various instances selected from the group comprising calcein, rhodamine, methylene blue and indocyanine green, for example indocyanine green.

According to various embodiments, the composition is suitable for oral administration, and comprises at least one active moiety presenting therapeutic, pharmaceutical, nutraceutical and/or cosmeceutical properties, in various instances a molecule presenting anticancerous properties, the at least one active moiety presenting therapeutic, pharmaceutical, nutraceutical and/or cosmeceutical properties being in the inner core of the nanocapsule.

According to various embodiments, the composition is suitable for topical administration, and comprises at least one cosmetic agent, in various instances an antioxidant, and/or at least one dermatological agent, in various instances a wound-healing agent, the at least one cosmetic agent being in the inner core of the nanocapsule.

According to various embodiments, the composition is suitable for loco-regional administration, and comprises at least one therapeutic and/or pharmaceutical agent, the at least one therapeutic and/or pharmaceutical agent being in the inner core of the nanocapsule.

The ninth object of the invention is directed to a method for manufacturing a negatively charged supported lipid bilayer on a positively charged mesoporous silica nanoparticle, the method comprising the following steps (a) preparing a first formulation of lipids, the lipids from the first formulation being 1,2 dioleoyl-sn-glycero-3-phospho-L-serine alias DOPS, cholesterol and at least one lipid different from DOPS and cholesterol, the first formulation of lipids being dissolved in a solvent; (b) preparing a second formulation of lipids, the lipids from the second formulation being 1,2-dioleoyl-3-trimethylammonium-propane alias DOTAP, cholesterol and at least one lipid different from DOTAP and cholesterol, the second formulation of lipids being dissolved in a solvent; and (c) mixing the first formulation with the second formulation at a temperature comprised between 40° C. and 60° C.; wherein the negatively charged supported lipid bilayer on a positively charged mesoporous silica nanoparticle has a potential comprised between −10 mV and −10 mV.

According to various embodiments, the number of equivalent of the DOTAP relative to one equivalent of DOPS is comprised between 0.5 and 1.5, in various instances is equal to 1.

According to various embodiments, the number of equivalents of cholesterol relative to one equivalent of DOPS is comprised between 2.30 and 2.70, in various instances is equal to 2.50.

According to various embodiments, the at least one lipid different from DOPS and cholesterol in step (a) is 1,2-dipalmitoyl-sn-glycero-3-phosphocholine alias DPPC.

According to various embodiments, the at least one lipid different from DOTAP and cholesterol in step (b) is 1,2-dipalmitoyl-sn-glycero-3-phosphocholine alias DPPC.

According to various embodiments, the number of equivalent of the DPPC relative to one equivalent of DOPS is comprised between 3.55 and 3.95, in various instances is equal to 3.75.

According to various embodiments, the solvent is a mixture of chloroform and methanol.

The tenth object of the invention is directed to a method for manufacturing a nanocapsule based on a negatively charged supported lipid bilayer on a positively charged mesoporous silica nanoparticle with a potential comprised between −10 mV and +10 mV, the method comprising the method in accordance with the ninth object of the invention followed by the steps of addition of an aqueous solution of sodium alginate; and the step of cross-linking of the sodium alginate.

According to various embodiments, the step of addition of alginate is performed by adsorption of an aqueous solution of sodium alginate at a concentration comprised between 1% (v/v) and 5% (v/v), in various instances at a concentration of 2% (v/v).

According to various embodiments, the step of cross-linking of the sodium alginate is performed by mixing an aqueous solution of calcium, at a concentration comprised between 40 mM and 60 mM, in various instances at a concentration of 50 mM.

The eleventh object of the invention is directed to a nanocapsule suitable for encapsulating at least one active moiety, the nanocapsule comprising an inner core, an inner layer and an outer layer, the inner core being formed by a mesoporous silica nanoparticle, the inner layer being formed by a lipid bilayer. The nanocapsule is remarkable in that the outer layer comprises cross-linked sodium alginate.

According to various embodiments, the outer layer of cross-linked sodium alginate has a thickness comprised between 3 nm and 100 nm, in various instances between 20 nm and 30 nm, for example 25 nm.

The twelfth object of the invention is directed to a composition comprising the nanocapsule in accordance with the eleventh object of the invention and at least one active moiety, the at least one active moiety being in the inner core of the nanocapsule.

According to various embodiments, the at least one active moiety is a contrasting agent in various instances selected from the group comprising calcein, rhodamine, methylene blue and indocyanine green, for example indocyanine green.

According to various embodiments, the composition is suitable for oral administration, and comprises at least one active moiety presenting therapeutic, pharmaceutical, nutraceutical and/or cosmeceutical properties, in various instances a molecule presenting anticancerous properties, the at least one active moiety presenting therapeutic, pharmaceutical, nutraceutical and/or cosmeceutical properties being in the inner core of the nanocapsule.

According to various embodiments, the composition is suitable for topical administration, and comprises at least one cosmetic agent, in various instances an antioxidant, and/or at least one dermatological agent, in various instances a wound-healing agent, the at least one cosmetic agent being in the inner core of the nanocapsule.

According to various embodiments, the composition is suitable for loco-regional administration, and comprises at least one therapeutic and/or pharmaceutical agent, the at least one therapeutic and/or pharmaceutical agent being in the inner core of the nanocapsule.

The invention is particularly interesting in that the reinforcement of the SLB allows for a better sealing of such nanocapsule and will also render them less or no permeable. The leaking issue will be suppressed or diminished. It will favour the stability and the slow-release of the active moiety, especially in presence of surfactants, inside of the nanocapsule.

The improvement of the stability is an advantage for incorporating those nanocapsules within creams, emulsions, creams based on emulsions, and hydrogel.

The method of the present invention will also render the nanocapsule more biocompatible, since the outer layer of the nanocapsule will be resistive at acidic pH. The drug release can be in this case better controlled.

As the slow-release of the active moiety is controlled by the outer layer of cross-linked alginate, various types of implementation of the nanocapsules according to the present invention can be derivatized. In particular, the slow and controlled release of hormonal product(s) and/or growth factor(s) can be envisioned with the nanocapsules in accordance with the present invention.

Various compositions that can be suitable for oral, topical, loco-regional administration could thus be developed.

DETAILED DESCRIPTION

The method of the invention consists in adding a cationic lipid onto a nanocapsule surrounded by a negatively charged lipid bilayer in order to be able to adsorb negatively charged polymer (such as sodium alginate) on nanocapsule surface. The first part of the method is performed by adding 1,2-dioleoyl-3-trimethylammonium-propane (DOTAP) in the form of liposome and by performing an ultra-sonication step. The step of ultra-sonication is essential since it will increase the temperature of the system and will allow the incorporation of DOTAP into the negatively charged supported lipid bilayer.

Figure 1:
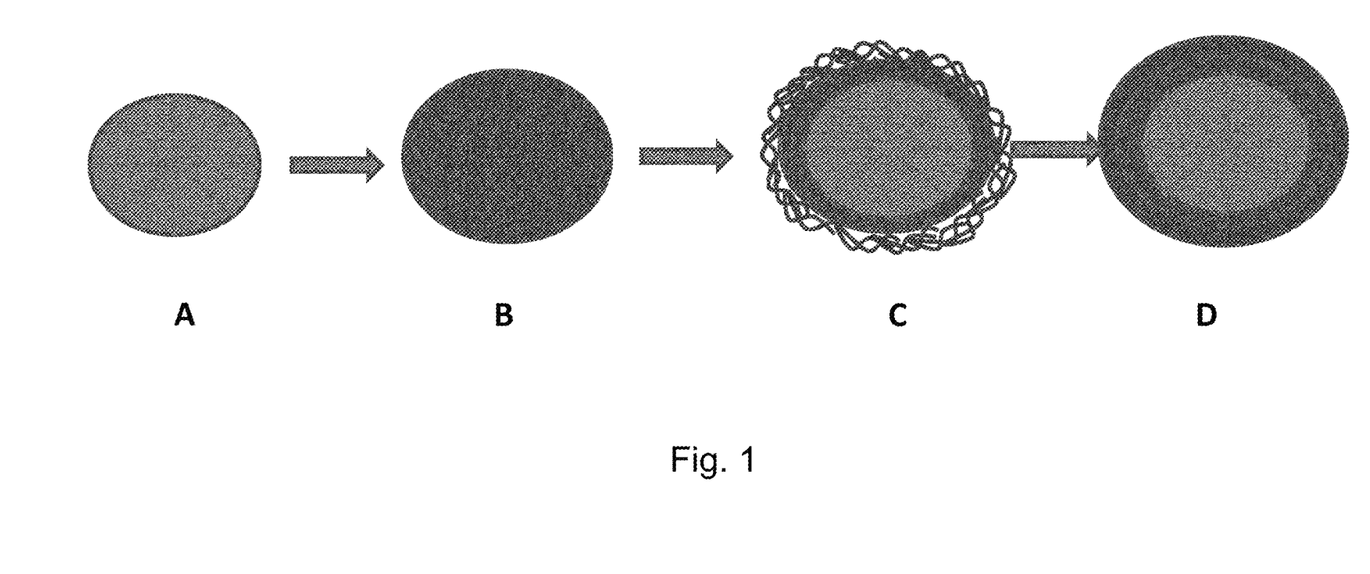
FIG. 1 is a general scheme showing the synthesis of nanocapsule in accordance with various embodiments of the present invention.

On FIG. 1, the nanocapsule A is a nanocapsule with an outer layer of negatively charged supported lipid bilayer.

In addition to the cholesterol, the SLB comprises a combination of various lipids and/or anionic and/or neutral phospholipids from the following list:
DPPG: 1,2-dihexadecanoyl-sn-glycero-3-phospho-(1'-rac-glycerol)
DOPG: 1,2-di-(9Z-octadecenoyl)-sn-glycero-3-phospho-(1'-rac-glycerol)
DOPS: 1,2-dioleoyl-sn-glycero-3-phospho-L-serine
DPPI: 1,2-dipalmitoyl-sn-glycero-3-phospho-(1'-myo-inositol)
DOPI: 1,2-dioleoyl-sn-glycero-3-phospho-(1'-myo-inositol)
DPPC: 1,2-dipalmitoyl-sn-glycero-3-phosphocholine
DOPC: 1,2-dioleoyl-sn-glycero-3-phosphocholine
DPPE: 1,2-dipalmitoyl-sn-glycero-3-phosphoethanolamine
DOPE: 1,2-dioleoyl-sn-glycero-3-phosphoethanolamine The nanocapsule B schematically shows that there was an incorporation of a layer of DOTAP. Any other cationic fatty acid chain might also be used.

The incorporation of DOTAP provides a nanocapsule with a supported lipid bilayer showing a ζ-potential comprised between −10 mV and +10 mV, so sensibly more positive than the nanocapsule with a SLB without such incorporation of DOTAP.

Advantageously, the ultra-sonication step can be carried out at a temperature comprised between 40° C. and 60° C., in order to promote the activation of the system and thus the incorporation of DOTAP into the outer layer.

Advantageously, the ultra-sonication step can be carried out during 10 minutes to 30 minutes. It is in various instances performed for a period of 20 minutes.

DOTAP is incorporated under the form of a liposome. The concentration of DOTAP in the liposome that is added is comprised between 50% and 150% of the concentration of at least one phospholipid (for example, DOPS) which is part the supported lipid bilayer. Advantageously, the concentration amounts to 100% of the concentration of the phospholipid.

Once DOTAP has been incorporated to the supported lipid bilayer protecting the nanoparticles, the electrostatic properties, demonstrated by the ζ-potential comprised between −10 mV and +10 mV, which control the adsorption of further components (ζ-potential is important to control the thickness of alginate layer and avoid the aggregation).

One example is the adsorption of alginate (see nanocapsule C of FIG. 1), or alginate derivatives, which are further cross-linked (see nanocapsule D of FIG. 1) in order to reinforce the structure of the outer layer of the nanocapsule.

Thus, the addition of an aqueous solution of sodium alginate is achieved, followed by a cross-linking step. The concentration of sodium alginate in the aqueous solution is relatively low, amounting to 1%-5% (by weight). In various instances, the concentration that is used is about 2% (by weight). In order to facility the adsorption, the nanocapsule can be placed in a solution of a buffering agent, for instance 4-(2-hydroxyethyl)-1-piperazineethanesulfonic acid (HEPES). In order to perform the cross-linking step, and to make a gel of sodium alginate, divalent cations are employed. Examples of compounds are $CaCl_2$ or $BaCl_2$. They can be in various instances used at a concentration comprised between 40 mM and 60 mM, for example at a concentration of 50 mM.

Therefore, nanocapsule suitable for encapsulating at least one active moiety can be made. Such nanocapsule comprises an inner core formed by a porous silica nanoparticle, in various instances a mesoporous silica nanoparticle, for example a positively charged mesoporous silica nanoparticle. The inner core is surrounded by an inner layer and an outer layer. The inner layer is formed by a supported lipid bilayer (SLB), in various instances a supported lipid bilayer comprising at least one phospholipid. The outer layer comprises cross-linked sodium alginate.

Moreover, the inner core can be formed by mica, clays, montmorillonite, alumina or $TiO_2$ particles. This allows for different manner of entrapping the active moiety.

The thickness of the outer layer made of cross-linked sodium alginate is comprised between 3 nm and 100 nm. It is in various instances comprised between 20 nm and 30 nm, for example it is equal to 25 nm.

Once the nanocapsule has been incubated with at least one active moiety, composition of all kinds can be obtained. The active moiety can be one contrasting agent, for instance calcein, rhodamine, methylene blue and/or indocyanine green. The active moiety can be one compound presenting therapeutic and/or pharmaceutical properties, for instance a molecule presenting anticancerous properties. The active moiety can also be one cosmetic agent, for instance an antioxidant. The incubation of the active moiety into the nanocapsule is performed before the encapsulation with the supported lipid bilayer and thus before the incorporation of DOTAP and the adsorption of alginate. Incubation of the active moiety is generally performed in milliQ water but can also be performed in citrate buffer.

In the implementation of a project related to the synthesis of mesoporous silica nanomaterials which are completely surrounded by supported lipid bilayer, the particular synthesis of negatively charged supported lipid bilayer (SLB) on a positively charged mesoporous silica nanoparticle MSNPs+) have been achieved. In the implementation of the process, the ζ-potential measured in milliQ water at a pH of 5.8 was inferior to −50 mV. The following paragraphs describe the synthesis of such nanocapsules with a highly negative ζ-potential.

Anionic supported lipid bilayers (SLB) on functionalized mesoporous silica nanoparticles (MSNPs) are synthesized in a one pot process using ultra-sonication. The ultra-sonication process allows indeed the incorporation of the MSNPs+ within the SLB.

The lipid formulations of supported lipid bilayer covering mesoporous silica nanoparticles were composed of 1,2-dioleoyl-sn-glycero-3-phospho-L-serine (DOPS), 1,2-dipalmitoyl-sn-glycero-3-phosphocholine (DPPC), and cholesterol.

When preparing the formulation, the lipids are dissolved in a solvent, in various instances a mixture of chloroform/methanol at a molar ratio of 9/1.

To form the thin lipid film, 1 ml of the formulation is then evaporated to remove the solvent.

The lipid film constituted by DPPC/DOPS/cholesterol was thus ultrasonicated in the presence of 4 ml of an aqueous solution of functionalized MSNPs with a nanoparticle size of 50.9±3.6 nm.

The concentration of the aqueous solution of functionalized MSNPs is fixed at 5 mg/mL.

Ultra-sonication of the lipid film in water induces very high shearing forces generating the formation of Small Unilamellar Vesicles (SUV) from MultiLamellar Vesicles (MLV).

At the end of the process, the stable colloidal suspension was then centrifuged to remove the excess of liposomes and the particles were suspended in water.

After formulation, lipids were extracted and then quantified using the Liquid Chromatography-Mass Spectrometry (LC-MS) method. Table I summarizes the different molar ratios for each lipid before and after the synthesis of the MSNPs incorporated within the SLB.

TABLE I

Initial molar ratios of each lipid before synthesis and final ratios after synthesis and purification of the MSNPs with SLB. The data are mean ± SE, performed by LC-MS in three independent experiments.

| | | DPPC | DOPS | cholesterol |
|---|---|---|---|---|
| Initial ratio | SLB | 52 | 14 | 34 |
| Ratio after synthesis | SLB | 41.5 ± 2.9 | 8.1 ± 2.3 | 50.3 ± 8.2 |

Variations can be seen between the lipids molar ratios before ultra-sonication and the final ratios found by LC-MS after the synthesis. The final molar ratio of cholesterol in the SLB increases from 34% to 50%.

This high amount of cholesterol (36%-50%) in the final SLB is necessary to give colloidal stability to the SLB. This is provided by the number of equivalents (2.50) of cholesterol relative to one equivalent of DOPS as initial molar ratio.

Figure 2:
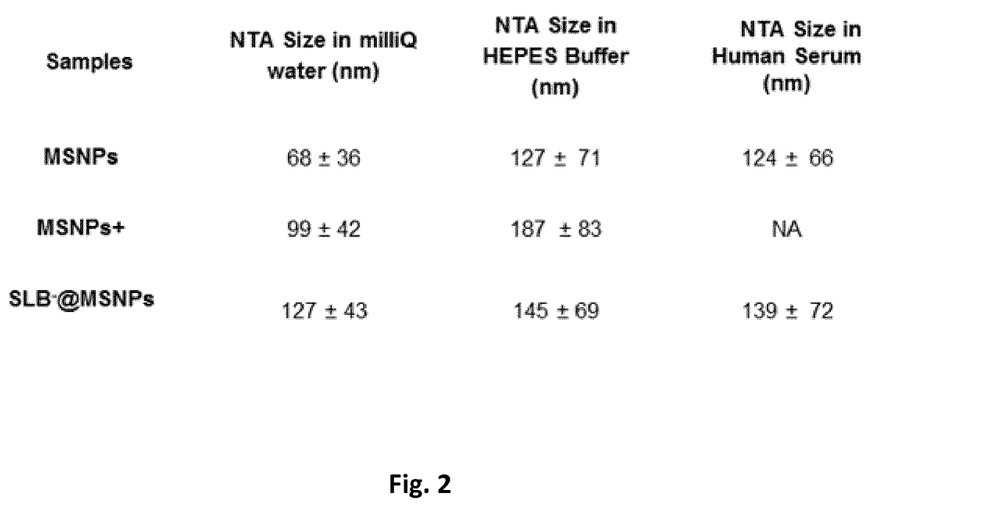
FIG. 2 is a size analysis of silica nanoparticles by Nano Tracking Analysis (NTA), in accordance with various embodiments of the present invention.
Figure 3:
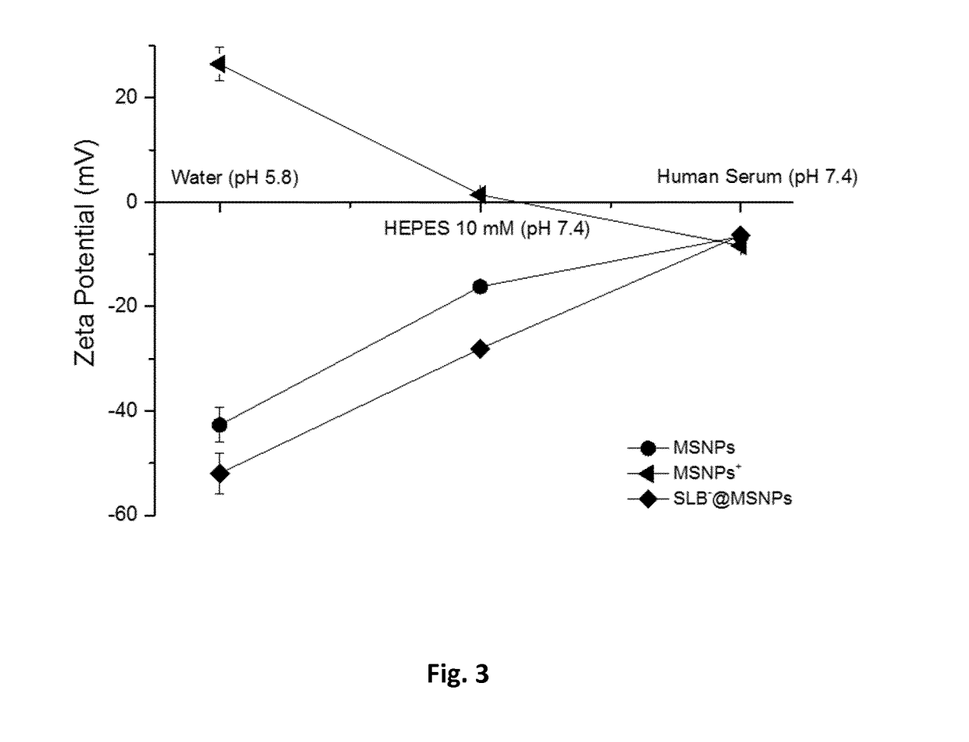
FIG. 3 is a ζ-potential graph for MSNPs, MSNPs+, and SLB on MSNPs performed on a Malvern instruments. Data are mean±SE and represent three independent experiments, in accordance with various embodiments of the present invention.

The ζ-potential properties of SLB on MSNPs were investigated in different media (milliQ water, HEPES buffer and human serum) and were compared with the similar physicochemical properties of MSNPs and MSNPs+(see FIGS. 2 and 3). These measurements have been made without performing any filtration or size exclusion prior to analysis. The size has been measured using NTA whereas ζ-potential has been measured by using Malvern Nano Zetasizer®. In milliQ water, at a pH value of 5.8, MSNPs+ have a charge of +26.47 mV whereas SLB on MSNPS have a charge of −52 mV.

Further details relating to the synthesis and use of the negatively charged supported lipid bilayer on a positively charged mesoporous silica nanoparticle are to be found in the International patent application numbered PCT/EP2016/067564.

In order to increase the ζ-potential, the method of the present invention has been applied on these highly negatively charged nanocapsules.

The method is exemplified herein: in a first alternative, directly after the centrifugation step (used to remove the excess of liposomes), a formulation comprising DOTAP liposomes is added. In a second alternative, a first formulation of lipids in a solvent can be prepared, on which a second formulation comprising DOTAP liposomes is added. The first formulation can for example comprise DOPS, cholesterol and at least one lipid different from DOPS and cholesterol, for instance DPPC.

The formulation of DOTAP liposomes comprises DOTAP, cholesterol and a lipid different from DOTAP and cholesterol, and is prepared in a solvent, in various instances in a mixture of chloroform/methanol 9/1. The overall concentration of the lipids in the solvent is comprised between 2 and 12 mg/l. The lipid different from DOTAP and cholesterol can be DPPC. The ratio DPPC/DOTAP/cholesterol can thus be 75/20/50. An evaporation of the solvent is performed in order to obtain a lipid film. After addition of about 5 mL of milliQ water, the suspension is then ultrasonicated. The excess of lipid aggregates was removed after centrifugation at 8000 rpm during 10 minutes by Eppendorff® 64R centrifuge. The DOTAP liposomes obtained were stored at 4° C. under argon. A ζ-potential value has been determined to be equal to +27.4±4 mV for this second formulation based on DOATP liposomes.

After addition of the formulation of DOTAP liposome on the highly negatively charged nanocapsules, an ultra-sonication step is carried out, in various instances at a temperature comprised between 40° C. and 60° C. This thermal activation (ultra-sonication and/or heating) is performed between 10 and 30 minutes, usually during 20 minutes.

ζ-potential measured by using Malvern Nano Zetasizer® in milliQ water, at a pH value of 5.8, is of −4.33±5 mV. That is the indication that the highly initial negative charge has been largely reduced, since now, the nanocapsule is almost bearing no charges at all.

The next step, concerning the adsorption and cross-linking, is thus carried out. An aqueous solution of sodium alginate is added, in various instances in a buffer based on HEPES). The concentration of sodium alginate is comprised between 1% and 5% by weight of the nanocapsule and is in various instances equal to 2%.

After the adsorption of sodium alginate, a calcium solution (based on $CaCl_2$)) was mixed with the nanocapsule suspension during 1 hour, resulting in a formation of a protective gel of alginate. A ζ-potential value has been determined to be equal to −15.1±3 mV after the formation of the gel.

Table II summarizes the different characteristics of the nanocapsule obtained according to the method of the present invention:

TABLE II

Size and ζ-potential of DOTAP liposomes, and the nanocapsules A, B, C and D as schematically represented on FIG. 1. The data are mean ± SE, performed in HEPES buffer.

| References on FIG. 1 | Composition of the samples | Size (nm)[1] | ζ-potential (mV)[2] |
|---|---|---|---|
| N/A[3] | liposomes DOTAP (DPPC/DOTAP/CHOL) | 70 ± 15 | +27.4 ± 4 |
| A | nanocapsule with DPPC/DOPS/CHOL | 120 ± 16 | −40 ± 10 |
| B | nanocapsule with at least DOPS + liposomes DOTAP | 172 ± 11 | −4.33 ± 5 |
| C | nanocapsule with at least DOPS + liposomes DOTAP + Alginate 2% | 168 ± 16 | −18.53 ± 6 |
| D | nanocapsule with at least DOPS + liposomes DOTAP + cross-linked Alginate 2% | 114 ± 15 | −15.1 ± 3 |

[1]Size obtained by Dynamic Light Scattering (DLS)
[2]ζ-potential obtained by DLS
[3]N/A = non-applicable These results indicate a weak aggregation of the nanocapsule obtained through the method of the present invention. The cross-linking of alginate with a calcium or barium cations also reduces the aggregation of the nanocapsules, since the average diameter is reduced. It is highlighted that the ζ-potential was highly negative at the beginning of the experiment and has become almost neutral once the DOTAP liposomes have been incorporated to the supported lipid bilayer.

Analysis of the nanocapsule has been made by cryo-TEM analysis. The average size is equal to 69±22 nm (as there is not solvatation layer apparent in the Cryo-TEM analysis, the average diameter size is smaller than the size measure by DLS, which is 114±15 nm).

Figure 4:
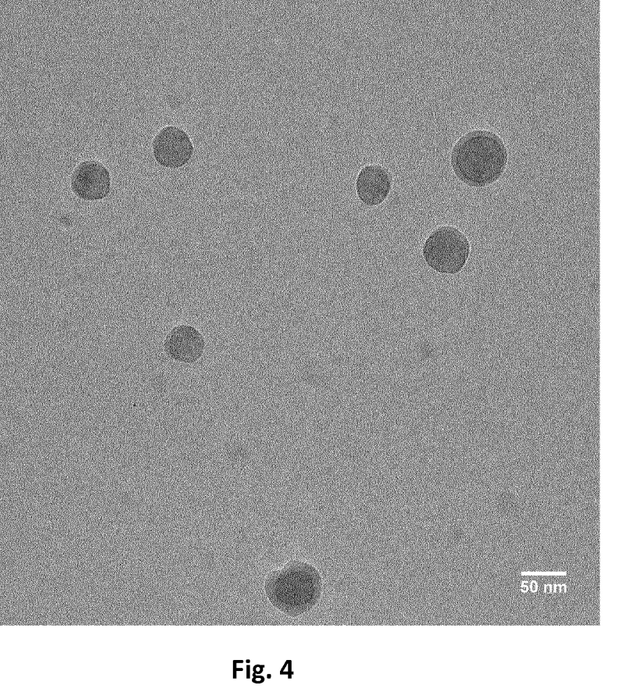
FIG. 4 is a Cryo-TEM image of a sample of nanocapsules with a cross-linked alginate as outer layer, in accordance with various embodiments of the present invention.

FIG. 4 shows an image Cryo-TEM. It demonstrates that no aggregation is present among the nanocapsule presenting an alginate gel as outer layer.

Figure 5:
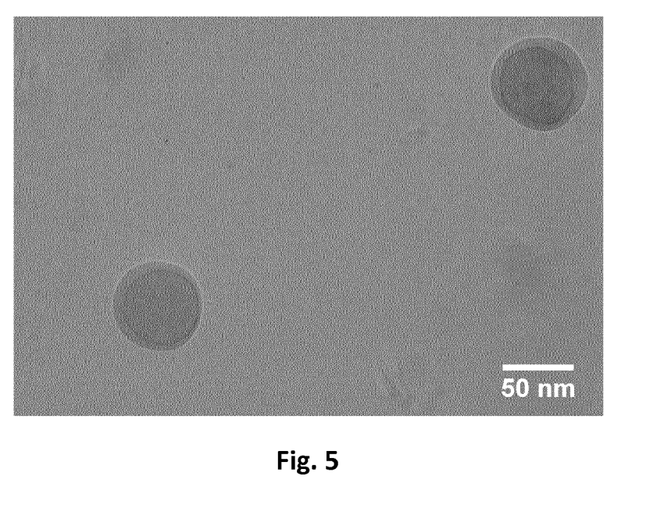
FIG. 5 is a Cryo-TEM image of two nanocapsules with a cross-linked alginate as outer layer, in accordance with various embodiments of the present invention.

FIG. 5 shows a detailed Cryo-TEM image, where two nanocapsules are present. The protective outer layer of alginate gel is clearly visible.

The leakage of the nanocapsule of the present invention was then studied. The fluorescent dye calcein was used in order to measure the properties of the nanocapsule to release or to hold the active moiety in its inner core which is a (meso)porous silica nanoparticle.

Table III shows the percentage of calcein leakage in the negatively charged supported lipid bilayer on a positively charged mesoporous silica nanoparticle (nanocapsule of the type A on FIG. 1), with a ζ-potential inferior or equal to −40 mV.

TABLE III

Leakage of calcein from highly negatively charged nanocapsules

| | % calcein leakage | | |
|---|---|---|---|
| Time in hours | HEPES | Cell medium | HEPES + 1% Triton X-100 |
| 2 h | 29 | 43 | 83 |
| 24 h | 38 | 50 | 96 |
| 48 h | 40 | 55 | 96 |
| 96 h | 43 | 67 | 96 |

Table IV shows the percentage of calcein leakage in the nanocapsule presenting an outer layer made of cross-linked alginate in accordance with the method of the present invention (nanocapsule of type D on Figure fig-ure 1).

TABLE IV

Leakage of calcein from nanocapsule in accordance with the present invention.

| | % calcein leakage | | | | |
|---|---|---|---|---|---|
| Time in hours | HEPES | Cell medium | pH 2 | HEPES + 1% Triton X-100 | HEPES + 1% MYRJ ™ S40 |
| 2 h | 25 | 26 | 9 | 37 | 37 |
| 24 h | 28 | 27 | 10 | 41 | 32 |
| 48 h | 28 | 28 | 10 | 41 | 31 |
| 96 h | 27 | 26 | 10 | 41 | 30 |

By comparison of tables III and IV, one can observe that the leakage of calcein is relatively more important in the case where the nanocapsule are not protected with an outer layer made of cross-linked alginate. Thus, the loss of active moiety is prevented when an outer layer of cross-linked alginate is present.

The implementations of such nanocapsules with the protective outer layer of cross-linked sodium alginate are various. Compositions comprising contrasting agents, therapeutic molecules, pharmaceutical agents, cosmetic agents, dermatological agents (wound-healing agents), anticancerous agents, nutraceutical agents, cosmeceutical agents, hormonal products, growth factors and/or compounds adapted for loco-regional therapies (bone implants and/or cardiac implants), for intraocular administration and/or for intratumoral agent, can be thus easily derivatized.

Experimental Section

Incubation of MSNP+ with excess of calcein in milliQ water

The incubation is performed with an amount of 1 mg of calcein for an amount of 2 mg of (meso)porous silica nanoparticles. The incubation is performed in milliQwater.

DOTAP Liposomes

Phospholipids were dissolved in chloroform/methanol 9:1 at a range of concentrations of 2 to 12 mg/mL. For DOTAP liposomes, the phospholipids ratio was DPPC/DOTAP/Cholesterol 75/20/50. Then, these lipids were evaporated to produce a lipid film. Five mL of milliQ water were mixed with the lipid film. The suspension was ultrasonicated with Ultrasonicator Sonics Vibra Cell® during 15 minutes at room temperature under Argon flow at 29% of amplitude pulsed mode 10 s/10 s. The excess of lipid aggregates was removed after centrifugation at 8 000 rpm during 10 minutes by Eppendorr 64R centrifuge. The DOTAP liposomes obtained were stored at 4° C. under Argon.

Aniocells

Phospholipids were dissolved in chloroform/methanol 9:1 at a range of concentrations of 2 to 12 mg/mL. For Aniocells, the phospholipids ratio was DPPC/DOPS/Cholesterol 75/20/50. Then, these lipids were evaporated to produce a lipid film. Five mL of calcein MSNP+ at 2 mg/mL were mixed with the lipid film. The suspension was ultrasonicated with Ultrasonicator Sonics Vibra Cell® during 15 minutes at room temperature under Argon flow at 29% of amplitude pulsed mode 10 s/10 s.

Ultra-Sonication of Aniocells and DOTAP Liposomes

The ultra-sonication step was carried out during 4 minutes at a pulse 10/10. The excess of liposomes (DOPS-DOTAP) was removed after centrifugation at 45 000 g, 20 minutes by Eppendorff® centrifuge. The aniocells-DOTAP liposomes was dispersed in HEPES buffer.

Adsorption of the Alginate Layer

The suspension of aniocells and DOTAP liposomes was mixed in presence of 2% alginate solution during 1 hour. The excess of alginate was removed after centrifugation at 45 000 g, 20 minutes by Eppendorff® centrifuge. The aniocells-DOTAP liposomes-aginate was dispersed in HEPES buffer.

Cross-Linking of the Alginate Layer 50 mM of calcium solution was mixed with the alginate suspension during 1 hour. The excess of calcium was removed after centrifugation at 45 000 g, 20 minutes by Eppendorff® centrifuge. The suspension was then dispersed in HEPES buffer.

LC-MS Experiments

The LC-MS Thermo Scientific Dionex BIO LC system is coupled with the mass of LTQ Orbitrap Elite. The system consisted of a GS50 gradient pump, AS50 Auto Sampler with oven column of thermal compartment. The separation was performed at 40° C. on a GRACE visionHT C18 HL column (150×2.1 mm i.d., 3 µm) from Dionex Bio LC with the scan mass of 300 and 1 000. The flow rate was 0.25 mL/min for the mobile phases (mobile phase C, 5 mM ammonium acetate in water (pH 4.0) and mobile phase D, 5 mM ammonium acetate in methanol). The binary linear gradient began from a mixture of 20% C and 80% D and ended at 100% D.

NTA Analysis

Nanoparticles Tracking Analysis (NTA) used a light scattering method which relates the rate of Brownian motion to particle size. This method allows direct and real time visualizing and analyzing of the NPs in liquids. During NTA measurement, NPs are illuminated by a focused laser beam and analyzed by the light scattered by each individual particle in the microscope onto the image sensor of a charge-coupled device (CCD) camera. The camera visualizes and records the frames of the particles in solution. The NTA software identifies and individually tracks the particles moving under Brownian motion. This measurement uses the temperature and the viscosity of the liquid to calculate particle size through the Stokes-Einstein equation. The Nanosight® analyses the particles with a size range from 30 to 1 µm. The samples were diluted at 0.01 mg/mL for analysis.

DLS Analysis

Malvern Nano Zetasizer® measures the size and ζ-potential of nanoparticles by using dynamic light scattering size (DLS). The analysis was performed with 0.1 mg/mL for each sample.

CryoTransmission Electron Microscopy (CRYO-TEM)

The purpose of the CRYO-TEM analysis is to determine the presence of the lipid bilayer surrounding silica NPs. The samples were frozen with liquid nitrogen in carbon grids by FEI Tool™ for sample preparation. Analyses were performed using FEI Titan Krios™ CRYO-TEM operated at 200 kV.

The invention claimed is:

1. A method for manufacturing supported lipid bilayer on a porous silica nanoparticle with a ζ-potential comprised between −10 mV and +10 mV, said method comprising the following steps:
    (a) providing a negatively charged supported lipid bilayer on a porous silica nanoparticle, wherein the negatively charged supported lipid bilayer has a ζ-potential less than −15 mV and wherein the negatively charged supported lipid bilayer comprises at least one phospholipid;
    (b) adding a formulation of lipids, the lipids being 1,2-dioleoyl-3-trimethylammonium-propane (DOTAP), cholesterol and at least one lipid different from DOTAP and cholesterol; and
    (c) performing an ultra-sonication.

2. The method according to claim 1, wherein the step (c) is carried out at a temperature between 40° C. and 60° C.

3. The method according to claim 1, wherein the concentration of DOTAP in the formulation of step (b) is between 50% and 150% of the concentration of the at least one phospholipid.

4. The method according to claim 1, wherein the step of ultra-sonication is performed for between 10 minutes and 30 minutes.

5. The method according to claim 1, wherein the at least one lipid different from DOTAP and cholesterol is 1,2-dipalmitoyl-sn-glycero-3-phosphocholine (DPPC).

6. The method according to claim 1, the method further comprising the following steps:
    (d) addition of an aqueous solution of sodium alginate; and
    (e) cross-linking of the sodium alginate to produce a nanocapsule.

7. The method according to claim 6, wherein the concentration of sodium alginate in the aqueous solution is between 1% (wt %) and 5% (wt %).

8. The method according to claim 6, wherein the addition is performed in a buffer solution, the buffer solution being 4-(2-hydroxyethyl)-1-piperazineethanesulfonic acid (HEPES) or on phosphate-buffered saline (PBS).

9. The method according to claim 6, wherein the step of cross-linking of the sodium alginate is performed by mixing an aqueous solution of divalent cation comprising calcium cation or barium cation, at a concentration between 40 mM and 60 mM.

10. The method according to claim 1, wherein the porous silica nanoparticle is a mesoporous silica nanoparticle.

11. A nanocapsule suitable for encapsulating at least one active moiety, the nanocapsule comprising an inner core, an inner layer and an outer layer, the inner core is a porous silica nanoparticle, the inner layer is a lipid bilayer, wherein the lipid bilayer comprises at least one phospholipid, and wherein the outer layer comprises cross-linked sodium alginate.

12. The nanocapsule according to claim 11, wherein the outer layer of cross-linked sodium alginate has a thickness comprised between 3 nm and 100 nm.

13. A composition comprising:
a nanocapsule, the nanocapsule suitable for encapsulating at least one active moiety and comprising an inner core, an inner layer and an outer layer, the inner core is a porous silica nanoparticle, the inner layer is a lipid bilayer, wherein the lipid bilayer comprises at least one phospholipid, wherein the outer layer comprises cross-linked sodium alginate, and at least one active moiety, the at least one active moiety being in the inner core of the nanocapsule.

14. The composition according to claim 13, wherein the at least one active moiety is one contrasting agent.

15. The composition according to claim 13 suitable for oral administration, the composition comprising the nanocapsule, and the at least one active moiety presents therapeutic, pharmaceutical, neutraceutical and/or cosmeceutical properties, the at least one active moiety being in the inner core of the nanocapsule.

16. The composition according to claim 13 suitable for topical administration, the composition comprising;
the nanocapsule; and
at least one of at least one cosmetic agent, and one dermatological agent being the at least one active moiety, the at least one of the at least one cosmetic agent and the at least one dermatological agent being in the inner core of the nanocapsule.

17. The composition according to claim 13 suitable for loco-regional administration, the composition comprising the nanocapsule, and the at least one active moiety presenting therapeutic and/or pharmaceutical properties.

18. The composition according to claim 14, wherein the one contrasting agent is selected from the group consisting of calcein, rhodamine, methylene blue and indocyanine green.

19. The composition according to claim 15, wherein the at least one active moiety is a molecule presenting anticancerous properties.

20. The composition according to claim 16, wherein the at least one cosmetic agent is an antioxidant, and the at least one dermatological agent is a wound-healing agent.

* * * * *